US012751696B2

(12) United States Patent
Kim et al.

(10) Patent No.: US 12,751,696 B2
(45) Date of Patent: Oct. 6, 2026

(54) ULTRASOUND IMAGING DEVICE INCLUDING DUAL MODE PROBE

(71) Applicant: EDGECARE INC., Seoul (KR)

(72) Inventors: Jung Jun Kim, Seoul (KR); Il Seob Song, Goyang-si (KR); Ji Hun Jang, Seoul (KR)

(73) Assignee: EDGECARE INC, Seoul (KR)

( * ) Notice: Subject to any disclaimer, the term of this patent is extended or adjusted under 35 U.S.C. 154(b) by 142 days.

(21) Appl. No.: 18/659,801

(22) Filed: May 9, 2024

(65) Prior Publication Data

US 2025/0017567 A1 Jan. 16, 2025

(30) Foreign Application Priority Data

Jul. 11, 2023 (KR) ........................ 10-2023-0089529

(51) Int. Cl.
*A61B 8/00* (2006.01)
*A61B 8/06* (2006.01)

(52) U.S. Cl.
CPC .............. *A61B 8/4477* (2013.01); *A61B 8/06* (2013.01); *A61B 8/4488* (2013.01); *A61B 8/488* (2013.01); *A61B 8/5223* (2013.01); *A61B 8/5246* (2013.01)

(58) Field of Classification Search
CPC ....... A61B 8/4477; A61B 8/06; A61B 8/4488; A61B 8/488; A61B 8/5223; A61B 8/5246; A61B 8/54; A61B 8/0891
See application file for complete search history.

(56) References Cited

U.S. PATENT DOCUMENTS

2010/0210946 A1* 8/2010 Harada ................ A61B 8/4281
600/443
2014/0303499 A1* 10/2014 Toma ..................... G16H 50/30
600/454
2018/0303462 A1* 10/2018 Lee ........................ A61B 8/488
(Continued)

FOREIGN PATENT DOCUMENTS

JP 2001198122 A 7/2001
KR 1020020087706 A 11/2002
KR 1020100080533 A 7/2010
(Continued)

*Primary Examiner* — Michael J Carey
*Assistant Examiner* — Zainab Mohammed Aldarraji
(74) *Attorney, Agent, or Firm* — ArentFox Schiff LLP

(57) ABSTRACT

The disclosure provides an ultrasound imaging device including a linear array, a first phased array, a second phased array, and a signal processing unit, wherein the linear array transmits and receives an image ultrasound signal to acquire an ultrasound image inside a human body; the first phased array provides a first Doppler ultrasound transmission signal to a vascular region included in the ultrasound image; and the second phased array provides a second Doppler ultrasound transmission signal to the vascular region; and an ultrasound imaging device including a dual-mode probe identifying a vascular region where blood vessels are located based on an ultrasound image acquired using a linear array at every predetermined time interval, focusing a Doppler ultrasound transmission signal on the vascular region using one or more phased arrays disposed on both sides of the linear array, and calculating a blood flow velocity by a received Doppler ultrasound reception signal.

10 Claims, 6 Drawing Sheets

(56) References Cited

U.S. PATENT DOCUMENTS

| | | | | |
|---|---|---|---|---|
| 2019/0008485 | A1* | 1/2019 | Li | G01S 15/8952 |
| 2024/0366969 | A1* | 11/2024 | Xu | A61B 8/5269 |

FOREIGN PATENT DOCUMENTS

| | | | |
|---|---|---|---|
| KR | 1020130139704 | A | 12/2013 |
| KR | 1020150027482 | A | 3/2015 |
| KR | 1020190044758 | A | 5/2019 |
| KR | 1020210032866 | A | 3/2021 |

* cited by examiner

[FIG. 1]
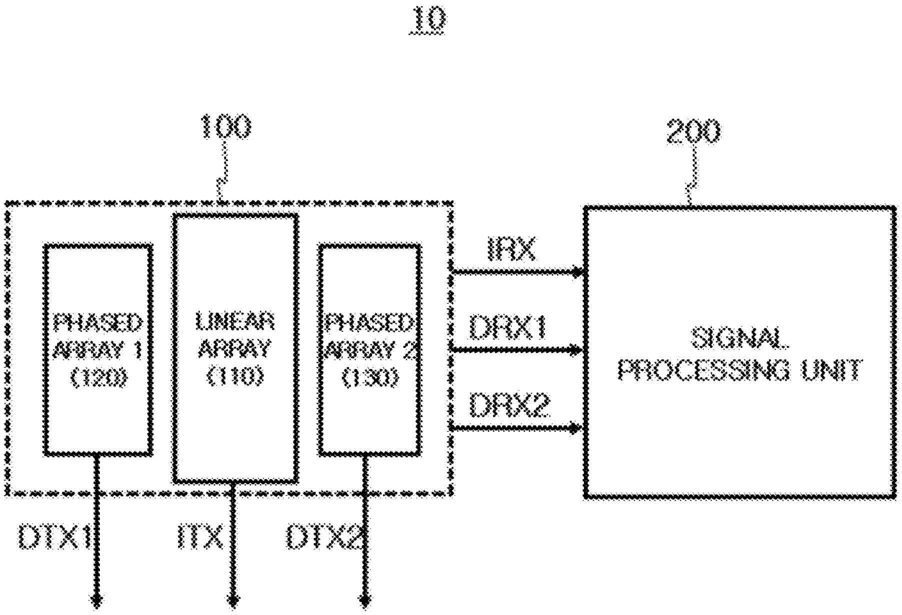
[FIG. 2]
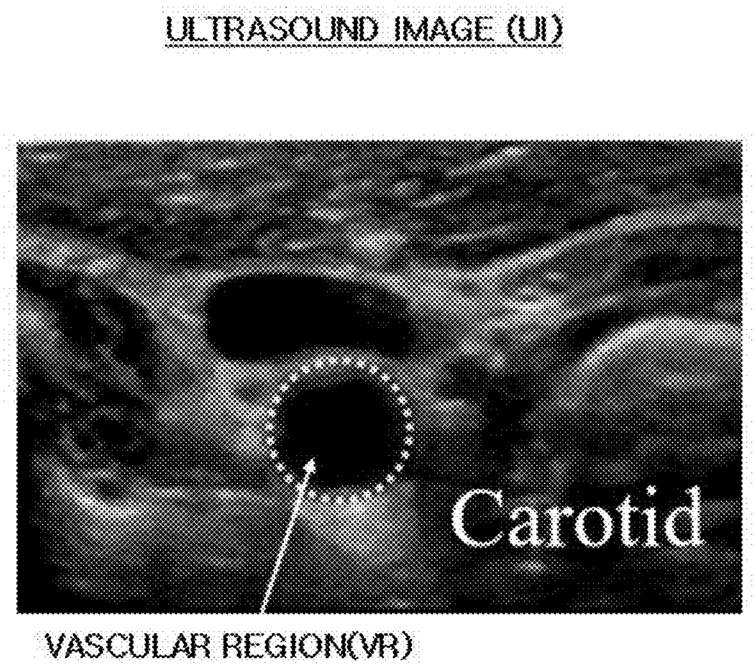

[FIG. 3]
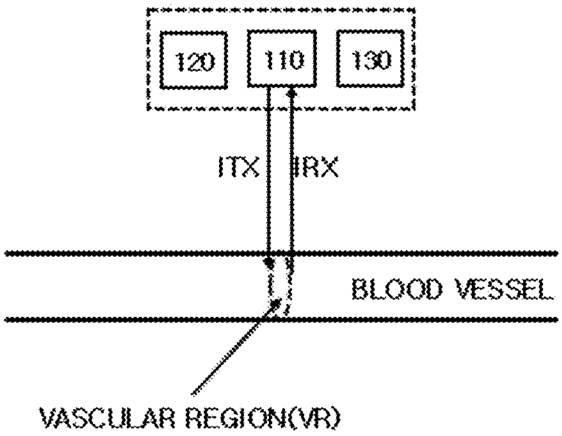
[FIG. 4]
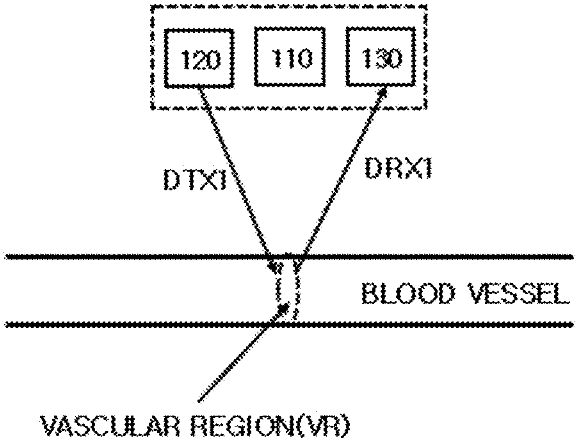

[FIG. 5]
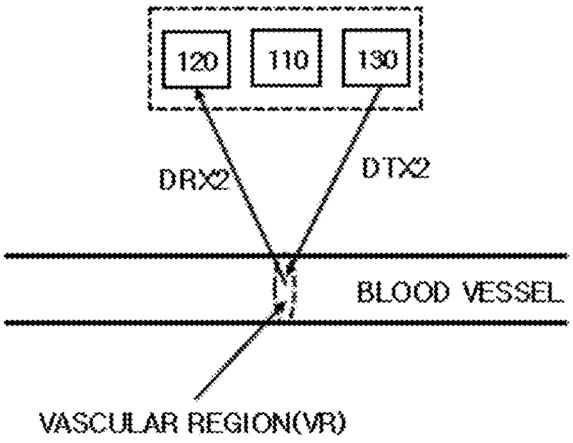
[FIG. 6]
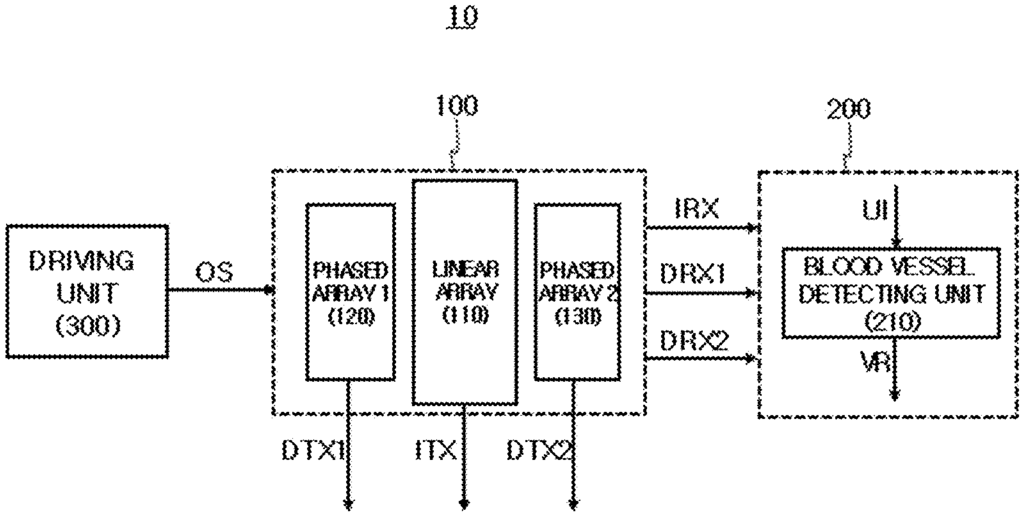
[FIG. 7]
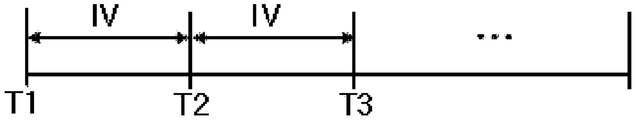

[FIG. 8]
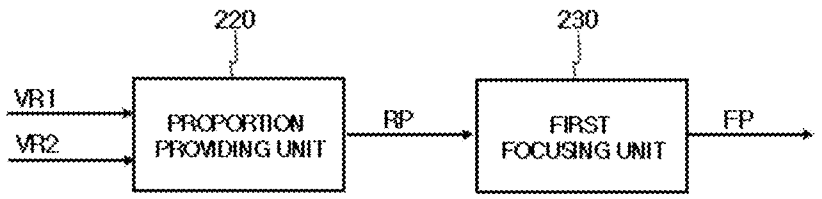
[FIG. 9]
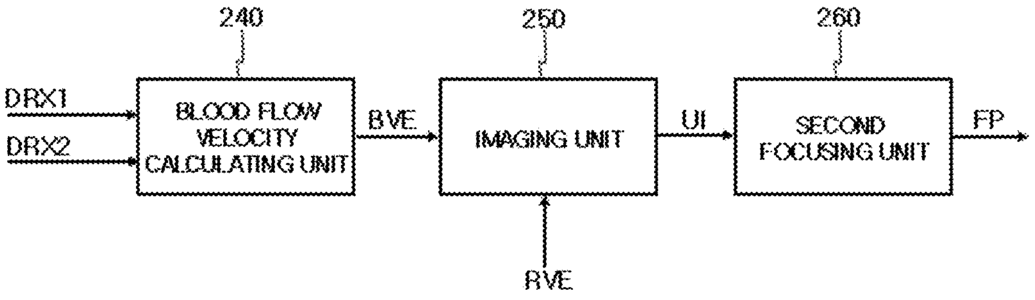
[FIG. 10]
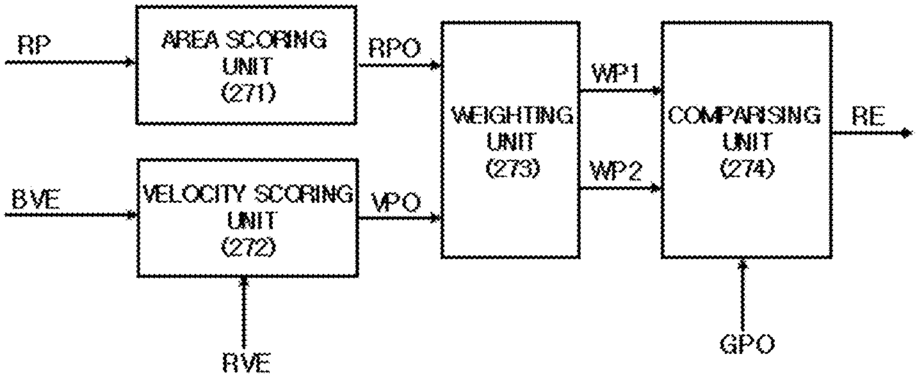

[FIG. 11]
| AREA PROPORTION (RP) | AREA SCORE(RPO) |
|---|---|
| 100% | 50 |
| 80% | 60 |
| 70% | 70 |
| 50% | 80 |
[FIG. 12]
| BLOOD FLOW VELOCITY (BVE) | VELOCITY SCORE(VPO) |
|---|---|
| 10 | 90 |
| 8 | 80 |
| 6 | 70 |
| 4 | 60 |
[FIG. 13]
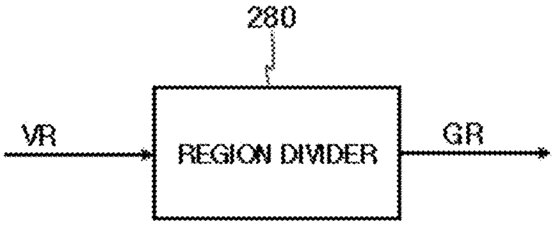

[FIG. 14]
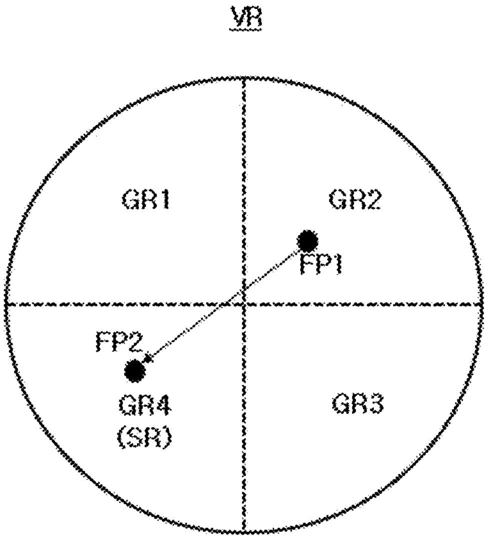

ULTRASOUND IMAGING DEVICE INCLUDING DUAL MODE PROBE

CROSS-REFERENCE TO RELATED APPLICATION

This application claims benefit of priority to Korean Patent Application No. 10-2023-0089529 filed on Jul. 11, 2023 in the Korean Intellectual Property Office, the contents of which are incorporated herein by reference in its entirety.

FIELD

The present disclosure relates to an ultrasound device including a dual mode probe.

BACKGROUND

In the case of measuring a blood flow velocity using ultrasound images, it may be difficult to accurately measure a blood flow velocity due to human movement. Recently, various types of research have been conducted to solve such a problem.

SUMMARY

An aspect of the present disclosure may provide an ultrasound imaging device including a dual-mode probe, capable of overcoming the difficulty of measuring a blood flow velocity due to human movement by identifying a vascular region in which blood vessels are located based on ultrasound images acquired using a linear array at every predetermined time interval, focusing a Doppler ultrasound transmission signal on the vascular region using one or more phased arrays disposed on both sides of the linear array, and calculating a blood flow velocity according to a received Doppler ultrasound reception signal.

An ultrasound imaging device according to an embodiment of the present disclosure may include a linear array, a first phased array, a second phased array, and a signal processing unit. The linear array may transmit and receive an image ultrasound signal to acquire an ultrasound image inside a human body. The first phased array may provide a first Doppler ultrasound transmission signal to a vascular region included in the ultrasound image. The second phased array may provide a second Doppler ultrasound transmission signal to the vascular region.

The first phased array may be disposed in a first direction with respect to the linear array, and the second phased array may be disposed in a second direction corresponding to a direction opposite to the first direction with respect to the linear array.

The ultrasound imaging device may include a driving unit and a blood vessel detecting unit. The driving unit may drive the linear array at every image interval corresponding to a predetermined time interval. The blood vessel detecting unit may detect the vascular region included in the ultrasound image acquired at each image interval.

The ultrasound imaging device may further include a proportion providing unit and a first focusing unit. The proportion providing unit may provide an area proportion overlapping between a first vascular region included in a first ultrasound image acquired at a first time by driving the linear array and a second vacular region included in a second ultrasound image acquired at a second time after an image interval from the first time. The first focusing unit may change focus positions of the first Doppler ultrasound transmission signal and the second Doppler ultrasound transmission signal according to the area proportion.

The second phased array may receive a first Doppler ultrasound reception signal in which the first Doppler ultrasound transmission signal provided from the first phased array or the linear array is reflected from the vascular region, and the first phased array may receive a second Doppler ultrasound reception signal in which the second Doppler ultrasound transmission signal provided from the second phased array or the linear array is reflected from the vascular region.

The ultrasound imaging device may further include a blood flow velocity calculating unit, an imaging unit, and a second focusing unit. The blood flow velocity calculating unit may calculate a blood flow velocity generated based on the first Doppler ultrasound reception signal and the second Doppler ultrasound reception signal. The imaging unit may drive the linear array to acquire the ultrasound image when the blood flow velocity is less than a predetermined reference velocity. The second focusing unit may focus the first Doppler ultrasound transmission signal and the second Doppler ultrasound transmission signal on a center of the vascular region included in the ultrasound image.

The ultrasound imaging device may further include an area scoring unit and a velocity scoring unit. The area scoring unit may provide an area score obtained by scoring the area proportion. The velocity scoring unit may provide a velocity score determined according to a difference between the blood flow velocity and the reference velocity.

The ultrasound imaging device may further include a weighting unit and a comparing unit. The weighting unit may determine a weight applied to each of the area score and the velocity score and providing a first weight score and a second weight score. The comparing unit may compare a sum of the first weight score and the second weight score with a predetermined reference score and providing a comparison result.

The ultrasound imaging device may further include a region divider. The region divider may divide the vascular region into a plurality of division regions.

When the sum of the first weight score and the second weight score is less than the reference score, the ultrasound imaging device may focus the first Doppler ultrasound transmission signal and the second Doppler ultrasound transmission signal on a selection region disposed farthest, among the division regions in the vascular region, from the positions on which the first Doppler ultrasound transmission signal and the second Doppler ultrasound transmission signal are focused.

In addition to the above-mentioned technical tasks of the present disclosure, other features and advantages of the present disclosure may be described below, or may be clearly understood by those skilled in the art to which the present disclosure pertains from such description and explanation.

According to the present disclosure as described above, the following effects are achieved.

The ultrasound imaging device including a dual-mode probe according to the present disclosure may identify a vascular region in which blood vessels are located based on an ultrasound image acquired using a linear array at every predetermined time interval, focus a Doppler ultrasound transmission signal on the vascular region using one or more phased arrays disposed on both sides of the linear array, and calculate a blood flow velocity according to a received Doppler ultrasound reception signal, thereby overcoming the difficulties of measuring a blood flow velocity due to human movement.

In addition, other features and advantages of the present disclosure may be newly understood through embodiments of the present disclosure.

BRIEF DESCRIPTION OF DRAWINGS

FIG. 1 is a diagram illustrating an ultrasound imaging device according to embodiments of the present disclosure.

FIG. 2 is a diagram illustrating a vascular region included in an ultrasound image acquired by the ultrasound imaging device of FIG. 1.

FIGS. 3 to 5 are diagrams illustrating the operations of the ultrasound imaging device of FIG. 1.

FIGS. 6 and 7 are diagrams illustrating an operation example of the ultrasound imaging device of FIG. 1.

FIG. 8 is a diagram illustrating a proportion providing unit and a first focusing unit included in the ultrasound imaging device of FIG. 1.

FIG. 9 is a diagram illustrating a blood flow velocity calculating unit, an imaging unit, and a second focusing unit included in the ultrasound imaging device of FIG. 1.

FIGS. 10 to 12 are diagrams illustrating an embodiment of the ultrasound imaging device of FIG. 1.

FIGS. 13 and 14 are diagrams illustrating another embodiment of the ultrasound imaging device of FIG. 1.

DETAILED DESCRIPTION

In the specification, in adding reference numerals to components throughout the drawings, it is to be noted that like reference numerals designate like components even though components are shown in different drawings.

Meanwhile, meanings of the terms described in this specification should be understood as follows.

Terms of singular forms used herein are intended to include their plural forms unless explicitly indicated otherwise, and a scope of the present disclosure is not limited by the terms used herein.

It is to be understood that a term "include" or "have" does not preclude the presence or addition of one or more other features, numerals, operations, components, parts or combinations thereof, which is mentioned in the specification.

Hereinafter, embodiments of the present disclosure are described in detail with reference to the accompanying drawings.

FIG. 1 is a diagram illustrating an ultrasound imaging device according to embodiments of the present disclosure, FIG. 2 is a diagram illustrating a vascular region included in an ultrasound image acquired by the ultrasound imaging device of FIG. 1, FIGS. 3 to 5 are diagrams illustrating the operations of the ultrasound imaging device of FIG. 1, and FIGS. 6 and 7 are diagrams illustrating an operation example of the ultrasound imaging device of FIG. 1.

Referring to FIGS. 1 to 7, an ultrasound imaging device 10 according to an embodiment of the present disclosure may include a linear array 110, one or more phased arrays, and a signal processing unit 200.

For example, the one or more phased arrays may include only a first phased array (phased array 1) 120 and a second phased array (phased array 2) 130 or may include both the first phased array 120 and the second phased array 130. The linear array 110 may transmit and receive image ultrasound signals to acquire an ultrasound image UI inside a human body. The linear array 110 may transmit an image ultrasound transmission signal ITX to the inside of the human body and receive an image ultrasound reception signal IRX reflected from the inside of the human body. The signal processing unit 200 included in the ultrasound imaging device 10 according to the present disclosure may implement an ultrasound image UI inside the human body based on the image ultrasound reception signal IRX. Here, the image ultrasound reception signal IRX reflected from the inside of the human body is expressed as being received by the linear array 110, but without being limited thereto, then image ultrasound reception signal IRX may be received through the first phased array 120 and the second phased array 130, and the signal processing unit 200 may implement an ultrasound image UI based on the image ultrasound reception signal IRX received through the first phased array 120 and the second phased array 130.

In an embodiment, the ultrasound imaging device 10 may include a driving unit 300 and a blood vessel detecting unit 210. The driving unit 300 may drive the linear array 110 at each image interval IV corresponding to a predetermined time interval. For example, the plurality of times may include a first time T1, a second time T2, and a third time T3. A time interval from the first time T1 to the second time T2 may be an image interval IV, and a time interval from the second time T2 to the third time T3 may also be an image interval IV.

The driving unit 300 included in the ultrasound imaging device 10 according to the present disclosure may drive the linear array 110 at the first time T1 to transmit the image ultrasound transmission signal ITX to the inside of the human body and receive the image ultrasound reception signal IRX reflected from the inside of the human body through the linear array 110. Thereafter, the image ultrasound reception signal IRX received by the linear array 110 may be implemented as a first ultrasound image UI1 in the signal processing unit 200.

In addition, after a time corresponding to the image interval IV from the first time T1 has elapsed, the driving unit 300 may drive the linear array 110 again at the second time T2 to transmit the image ultrasound transmission signal ITX to the inside of the human body and receive the image ultrasound reception signal IRX reflected from the inside of the human body through the linear array 110. Thereafter, the image ultrasound reception signal IRX received by the linear array 110 may be implemented as a second ultrasound image UI2 in the signal processing unit 200.

The blood vessel detecting unit 210 may detect a vascular region VR included in the ultrasound image UI acquired at every image interval IV. For example, the blood vessel detecting unit 210 may analyze the first ultrasound image UI1 and the second ultrasound image UI2 to detect the vascular region VR corresponding to respective regions in which blood vessels are located.

Thereafter, the first phased array 120 may provide a first Doppler ultrasound transmission signal DTX1 to the vascular region VR included in the ultrasound image UI. For example, the first phased array 120 may transmit the first Doppler ultrasound transmission signal DTX1 to the center of the vascular region VR detected through the blood vessel detecting unit 210, and the first Doppler ultrasound reception signal DRX1 reflected from the vascular region VR may be received by the first phased array 120 or the second phased array 130. The signal processing unit 200 included in the ultrasound imaging device 10 according to the present disclosure may calculate a blood flow velocity BE in the vascular region VR using the first Doppler ultrasound reception signal DRX1 received by the first phased array 120 or the second phased array 130.

The second phased array 130 may provide a second Doppler ultrasound transmission signal DTX2 to the vascular region VR. For example, the second phased array 130 may transmit the second Doppler ultrasound transmission signal DTX2 to the center of the vascular region VR detected through the blood vessel detecting unit 210, and the second Doppler ultrasound reception signal DRX2 reflected from the vascular region VR may be received by the first phased array 120 or the second phased array 130. The signal processing unit 200 included in the ultrasound imaging device 10 according to the present disclosure may calculate the blood flow velocity BVE in the vascular region VR using the second Doppler ultrasound reception signal DRX2 received by the first phased array 120 or the second phased array 130.

Here, transmission of the Doppler ultrasound transmission signal using the first phased array 120 and the second phased array 130 is described, but the blood flow velocity BE in the vascular region VR may also be calculated by transmitting the Doppler ultrasound transmission signal to the vascular region VR using the linear array 110 and receiving the Doppler ultrasound reception signal reflected from the vascular region VR by the first phased array 120 or the second phased array 130. For example, the blood flow velocity BE in the vascular region VR may be calculated by transmitting the Doppler ultrasound transmission signal to the vascular region VR using some elements included in the linear array 110 and receiving the Doppler ultrasound reception signal reflected from the vascular region VR through the first phased array 120. In addition, when the vascular region VR moves due to human movement, etc., positions of elements of the linear array 110 corresponding to the vascular region VR before movement and positions of the elements of the linear array 110 corresponding to the vascular region after movement may be different. In this case, the blood flow velocity BE in the vascular region VR may also be calculated using some elements of the linear array 110 corresponding to the vascular region VR after movement.

In an embodiment, the first phased array 120 may be disposed in a first direction DR1 with respect to the linear array 110, and the second phased array 130 may be disposed in a second direction DR2, which is opposite to the first direction DR1, based on the linear array 110. For example, the first phased array 120 may be disposed on the left with respect to the linear array 110, and the second phased array 130 may be disposed on the right with respect to the linear array 110. Here, the first direction DR1 may be left, and the second direction DR2 may be right.

The ultrasound imaging device 10 including a dual-mode probe according to the present disclosure may identify the vascular region VR in which blood vessels are located based on the ultrasound image UI acquired using the linear array 110 at every predetermined time interval, focus the Doppler ultrasound transmission signal on the vascular region VR using one or more phased arrays disposed on both sides of the linear array 110, and calculate the blood flow velocity BVE according to the received Doppler ultrasound reception signal, thereby overcoming the difficulties in measuring the blood flow velocity BVE due to human movement.

FIG. 8 is a diagram illustrating a proportion providing unit and a first focusing unit included in the ultrasound imaging device of FIG. 1, and FIG. 9 is a drawing illustrating a blood flow velocity calculating unit, an imaging unit, and a second focusing unit included in the ultrasound imaging device of FIG. 1.

Referring to FIGS. 1 to 9, the ultrasound imaging device 10 may further include a proportion providing unit 220 and a first focusing unit 230. The proportion providing unit 220 may drive the linear array 110 to provide an area proportion RP overlapping between a first vascular region VR1 included in the first ultrasound image UI1 acquired at the first time T1 and a second vascular regions VR2 included in the second ultrasound image UI2 acquired at the second time T2 after the image interval IV from the first time T1. For example, a position of the first vascular region VR1 included in the first ultrasound image UI1 and a position of the second vascular region VR2 included in the second ultrasound image UI2 may be different. In this case, the first vascular region VR1 and the second vascular region VR2 may not overlap 100%.

Here, a predetermined reference proportion may be 95%. When the overlapping proportion of the first vascular region VR1 and the second vascular region VR2 is less than the reference proportion, the first focusing unit 230 may determine that the movement of the vascular region VR is large and move focus positions of the first Doppler ultrasound transmission signal DTX1 and the second Doppler ultrasound transmission signal DTX2 to the center of the second vascular region VR2. In addition, when the overlapping proportion of the first vascular region VR1 and the second vascular region VR2 is greater than the reference proportion, the first focusing unit 230 may determine that the movement of the vascular region VR is small and may not move the focus positions of the first Doppler ultrasound transmission signal DTX1 and the second Doppler ultrasound transmission signal DTX2 to the center of the second vascular region VR2.

In an embodiment, the first focusing unit 230 may change the focus positions of the first Doppler ultrasound transmission signal DTX1 and the second Doppler ultrasound transmission signal DTX2 according to the area proportion RP.

In an embodiment, the second phased array 130 may receive the first Doppler ultrasound reception signal DRX1 in which the first Doppler ultrasound transmission signal DTX1 provided from the first phased array 120 or the linear array 110 is reflected from the vascular region VR, and the first phased array 120 may receive the second Doppler ultrasound reception signal DRX2 in which the second Doppler ultrasound transmission signal DTX2 provided from the second phased array 130 or the linear array 110 is reflected from the vascular region VR.

FIGS. 10 to 12 are diagrams illustrating an embodiment of the ultrasound imaging device of FIG. 1.

Referring to FIGS. 1 to 12, in an embodiment, the ultrasound imaging device 10 may further include a blood flow velocity calculating unit 240, an imaging unit 250, and a second focusing unit 260. The blood flow velocity calculating unit 240 may calculate the blood flow velocity BVE generated based on the first Doppler ultrasound reception signal DRX1 and the second Doppler ultrasound reception signal DRX2. For example, the first Doppler ultrasound reception signal DRX1 may represent a signal received by the first phased array 120 or the second phased array 130 after the first Doppler ultrasound transmission signal DTX1 transmitted from the first phased array 120 is reflected from the vascular region VR, and the second Doppler ultrasound reception signal DRX2 may represent a signal received by the first phased array 120 or the second phased array 130 after the second Doppler ultrasound transmission signal DTX2 transmitted from the second phased array 130 is reflected from the vascular region VR. The blood flow velocity calculating unit 240 included in the ultrasound imaging device 10 according to the present disclosure may calculate the blood flow velocity BE in the vascular region VR using the first Doppler ultrasound reception signal DRX1 and the second Doppler ultrasound reception signal DRX2.

If the blood flow velocity BVE is less than the predetermined reference velocity RVE, the imaging unit 250 may drive the linear array 110 to acquire the ultrasound image UI. For example, due to human movement, a point focused using the first phased array 120 and the second phased array 130 may deviate from the blood vessel, and the blood flow velocity BVE calculated by the blood flow velocity calculating unit 240 may be less than the reference velocity RVE. In this case, the imaging unit 250 included in the ultrasound imaging device 10 according to the present disclosure may acquire the ultrasound image UI by driving the linear array 110 to re-identify the position of the vascular region VR.

In addition, in an embodiment, when a magnitude of a signal at a position corresponding to a blood vessel wall in one scan line acquired at every predetermined regular time interval is less than the predetermined reference size, the ultrasound imaging device 10 according to the present disclosure may transmit an image ultrasound transmission signal to an object, receive an image ultrasound reception signal reflected from the object to acquire the ultrasound image UI, and re-identify the position of the moved vascular region VR.

The second focusing unit 260 may focus the first Doppler ultrasound transmission signal DTX1 and the second Doppler ultrasound transmission signal DTX2 on the center of the vascular region VR included in the ultrasound image UI. For example, when the vascular region VR that has moved due to human movement is detected through the imaging unit 250, the second focusing unit 260 may focus the first Doppler ultrasound transmission signal DTX1 and the second Doppler ultrasound transmission signal DTX2 based on the moved vascular region VR.

In an embodiment, the ultrasound imaging device 10 may further include an area scoring unit 271 and a velocity scoring unit 272. The area scoring unit 271 may provide an area score RPO acquired by scoring the area proportion RP. The area scoring unit 271 may be configured to reduce the area score RPO as the area proportion RP in which the first vascular region VR1 included in the first ultrasound image UI1 and the second vascular region VR2 included in the second ultrasound image UI2 overlap increases. For example, when the area proportion RP is 100%, the area score RPO may be 50 points, and when the area proportion RP is 80%, the area proportion RPO may be 60 points. In addition, when the area proportion RP is 70%, the area score RPO may be 70 points, and when the area proportion RP is 50%, the area score RPO may be 80 points.

The velocity scoring unit 272 may provide a velocity score VPO determined according to a difference value between the blood flow velocity BVE and the reference velocity RVE. The velocity scoring unit 272 may be configured so that the velocity score VPO increases as the blood flow velocity BVE in the vascular region VR increases. For example, the reference velocity RVE may be 5. When the blood flow velocity BVE is 10, the velocity score VPO may be 90 points, and when the blood flow velocity BVE is 8, the velocity score VPO may be 80 points. In addition, when the blood flow velocity BVE is 6, the velocity score VPO may be 70 points, and when the blood flow velocity BVE is 4, the velocity score VPO may be 60 points. Here, the velocity score VPO is described as being determined according to the blood flow velocity BVE calculated based on the Doppler signal and reference velocity RVE, but may also be determined according to the energy of the Doppler signal and reference energy (threshold).

In an embodiment, the ultrasound imaging device 10 may further include a weighting unit 273 and a comparing unit 274. The weighting unit 273 may determine a weight applied to each of the area point RPO and the velocity score VPO and provide a first weight score WP1 and a second weight score WP2. For example, the weight may be set to vary depending on the user's settings. The first weight score WP1 may be a score obtained by applying the weight to the area score RPO, and the second weight score WP2 may be a score obtained by applying the weight to the velocity score VPO.

The comparing unit 274 may compare the sum of the first weight score WP1 and the second weight score WP2 with a predetermined reference score GPO and provide a comparison result RE. For example, the weight applied to each of the area score RPO and velocity score VPO may be 1, the first weight score WP1 may be 50 points, and the second weight score WP2 may be 60 points. Here, the reference score may be 120 points. In this case, 110 points, which is the sum of the first weight score WP1 and the second weight score WP2, may be less than the reference score of 120 points.

If the sum of the first weight score WP1 and the second weight score WP2 is less than the reference score, the comparing unit 274 may determine that part of the vascular region VR is blocked. For example, the blood flow velocity BE appearing to be relatively low in spite of the area proportion RP to the vascular region VR maintained at 100% due to the absence of human movement may mean that the first Doppler ultrasound transmission signal DTX1 and the second Doppler ultrasound transmission signal DTX2 are focused on part in which stationary materials are piled up in the vascular region VR.

FIGS. 13 and 14 are diagrams illustrating another embodiment of the ultrasound imaging device of FIG. 1.

In an embodiment, the ultrasound imaging device 10 may further include a region divider 280. The region divider 280 may divide the vascular region VR into a plurality of division regions. For example, the region divider 280 may divide the vascular region VR into a first division region GR1 to a fourth division region GR4. A point on which the first Doppler ultrasound transmission signal DTX1 and the second Doppler ultrasound transmission signal DTX2 are focused is the second division region of the vascular region VR, and when wastes are accumulated in the second division region, the sum of the first weight score WP1 and the second weight score WP2 may be less than the reference score.

In an embodiment, when the sum of the first weight score WP1 and the second weight score WP2 is less than the reference score GPO, the ultrasound imaging device 10 may focus the first Doppler ultrasound transmission signal DTX1 and the second Doppler ultrasound transmission signal DTX2 from a position to which the first Doppler ultrasound transmission signal DTX1 and the second Doppler ultrasound transmission signal DTX2 are focused to a selection region SR located farthest among the division regions in the vascular region VR. For example, the division region located farthest from the second division region GR2 may be the fourth division region GR4, and the ultrasound imaging device 10 according to the present disclosure may set the fourth division region GR4 as the selection region SR and transmit the first Doppler ultrasound transmission signal DTX1 and the second Doppler ultrasound transmission signal DTX2 to the selection region SR.

The ultrasound imaging device 10 including a dual-mode probe according to the present disclosure may identify the vascular region VR in which blood vessels are located based on the ultrasound image UI acquired using the linear array 110 at every predetermined time interval, focus the Doppler ultrasound transmission signal on the vascular region VR using one or more phased arrays disposed on both sides of the linear array 110, and calculate the blood flow velocity BE according to the received Doppler ultrasound reception signal, thereby overcoming the difficulties of measuring the blood flow velocity due to human movement.

In addition to the above-mentioned technical tasks of the present disclosure, other features and advantages of the present disclosure may be described below, or may be clearly understood by those skilled in the art to which the present disclosure pertains from such description and explanation.

The invention claimed is:

1. An ultrasound imaging device comprising:

a linear array transmitting and receiving an image ultrasound signal to acquire an ultrasound image inside a human body;

one or more phased arrays providing a Doppler ultrasound transmission signal to a vascular region included in the ultrasound image; and a region divider dividing the vascular region into a plurality of division regions;

wherein, the one or more phased array comprises a first phased array providing a first Doppler ultrasound transmission signal to the vascular region included in the ultrasound image and a second phased array providing a second Doppler ultrasound transmission signal to the vascular region; and the ultrasound imaging device focuses the first Doppler ultrasound transmission signal and the second Doppler ultrasound transmission signal on a selection region disposed farthest, among the division regions of the vascular region, from the positions on which the first Doppler ultrasound transmission signal and the second Doppler ultrasound transmission signal are focused.

2. The ultrasound imaging device of claim 1, wherein the first phased array is disposed in a first direction with respect to the linear array, and the second phased array is disposed in a second direction corresponding to a direction opposite to the first direction with respect to the linear array.

3. The ultrasound imaging device of claim 2, further comprising:

a driving processor configured to drive the linear array at every image interval corresponding to a predetermined time interval; and a blood vessel detecting processor configured to detect the vascular region included in the ultrasound image acquired at each image interval.

4. The ultrasound imaging device of claim 3, further comprising:

a proportion providing processor configured to provide an area proportion overlapping between a first vascular region included in a first ultrasound image acquired at a first time by driving the linear array and second vacular region included in a second ultrasound image acquired at a second time after an image interval from the first time; and a first focusing processor configured to change focus positions of the first Doppler ultrasound transmission signal and the second Doppler ultrasound transmission signal according to the area proportion.

5. The ultrasound imaging device of claim 4, wherein the second phased array receives a first Doppler ultrasound reception signal in which the first Doppler ultrasound transmission signal provided from the first phased array or the linear array is reflected from the vascular region, and the first phased array receives a second Doppler ultrasound reception signal in which the second Doppler ultrasound transmission signal provided from the second phased array or the linear array is reflected from the vascular region.

6. The ultrasound imaging device of claim 5, further comprising:

a blood flow velocity calculating processor configured to calculate a blood flow velocity generated based on the first Doppler ultrasound reception signal and the second Doppler ultrasound reception signal;

an imaging processor configured to drive the linear array to acquire the ultrasound image when the blood flow velocity is less than a predetermined reference velocity; and a second focusing processor configured to focus the first Doppler ultrasound transmission signal and the second Doppler ultrasound transmission signal on a center of the vascular region included in the ultrasound image.

7. The ultrasound imaging device of claim 6, further comprising:

an area scoring processor configured to provide an area score obtained by scoring the area proportion; and a velocity scoring processor configured to provide a velocity score determined according to a difference between the blood flow velocity and the reference velocity.

8. The ultrasound imaging device of claim 7, further comprising:

a weighting unit determining a weight applied to each of the area score and the velocity score and providing a first weight score and a second weight score; and a comparing unit comparing a sum of the first weight score and the second weight score with a predetermined reference score and providing a comparison result.

9. The ultrasound imaging device of claim 8, the sum of the first weight score and the second weight score is less than the reference score.

10. The ultrasound imaging device of claim 6, further comprising:

a velocity scoring processor configured to provide a velocity score determined according to energy of the first Doppler ultrasound reception signal and the second Doppler ultrasound reception signal and a predetermined reference energy.

* * * * *